US006123070A

United States Patent [19]

Bruna et al.

[11] Patent Number: 6,123,070

[45] Date of Patent: Sep. 26, 2000

[54] DEVICE FOR ENHANCING THE EMPTYING OF AN INHALER METERING CHAMBER

[75] Inventors: Pascal Bruna, Rouen, France; Giuseppe Stradella, Camogli, Italy

[73] Assignee: Valois S.A., Le Neuborg, France

[21] Appl. No.: 08/973,150

[22] PCT Filed: Jun. 7, 1996

[86] PCT No.: PCT/FR96/00860

§ 371 Date: Feb. 9, 1998

§ 102(e) Date: Feb. 9, 1998

[87] PCT Pub. No.: WO96/41650

PCT Pub. Date: Dec. 27, 1996

[51] Int. Cl.[7] .......................... A61M 15/00; A61M 15/08

[52] U.S. Cl. ................................ 128/203.15; 128/203.12; 128/203.23

[58] Field of Search ......................... 128/203.12, 203.15, 128/200.14, 200.23, 203.23

[56] References Cited

U.S. PATENT DOCUMENTS

| | | | |
|---|---|---|---|
| 1,732,566 | 10/1929 | McKendrick | 128/203.28 |
| 3,522,659 | 8/1970 | Welch | 34/22 |
| 5,295,479 | 3/1994 | Lankinen | 128/203.15 |
| 5,388,572 | 2/1995 | Mulhauser et al. | 128/203.15 |
| 5,394,868 | 3/1995 | Ambrosio . | |
| 5,533,505 | 7/1996 | Kallstrand et al. | 128/203.15 |
| 5,579,758 | 12/1996 | Century | 128/200.22 |

FOREIGN PATENT DOCUMENTS

| | | | |
|---|---|---|---|
| 92/00771 | 1/1992 | WIPO | A61M 15/00 |
| 9217233 | 10/1992 | WIPO . | |
| 9318812 | 9/1993 | WIPO . | |
| 9503846 | 2/1995 | WIPO . | |

*Primary Examiner*—John G. Weise
*Assistant Examiner*—Todd M. Martin
*Attorney, Agent, or Firm*—Sughrue, Mion, Zinn, Macpeak & Seas, PLLC

[57] ABSTRACT

A device is provided for emptying a metering chamber of a powder dispenser. The dispenser includes an expulsion channel passing through the metering chamber and a device for delivering an air flow which is intended to pass along the expulsion channel to empty the metering chamber when the dispenser is actuated. A flow device is adapted to configure the air flow in such a manner that it empties the metering chamber completely. The flow device is disposed in the expulsion channel upstream from the metering chamber in the flow direction of the air flow.

24 Claims, 4 Drawing Sheets

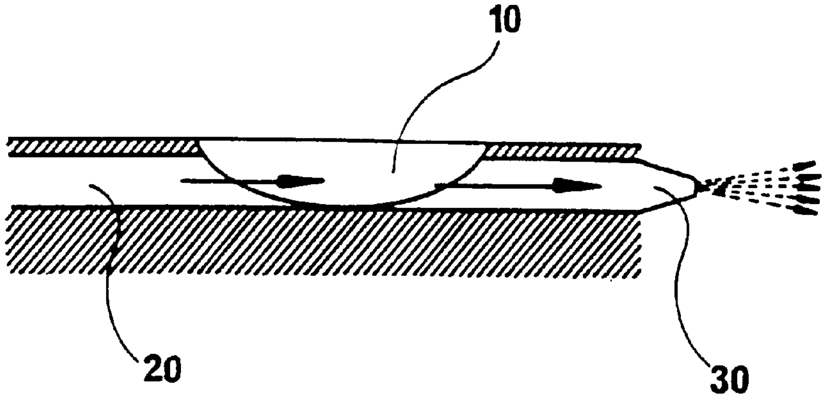
FIG.1
PRIOR ART
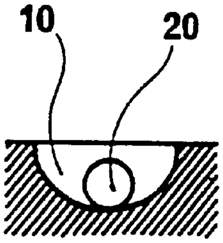
FIG.2
PRIOR ART
PRIOR ART
FIG.3
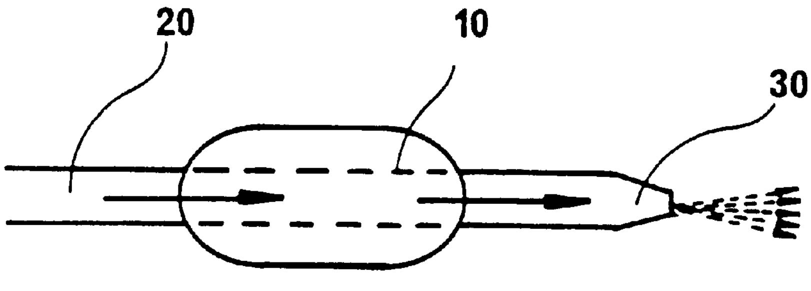

DEVICE FOR ENHANCING THE EMPTYING OF AN INHALER METERING CHAMBER

The present invention relates to a device for making it easier to empty a metering chamber of a powder dispenser, and in particular of a powder inhaler.

The use of powder inhalers is now widespread, particularly in the pharmaceutical field, and requirements concerning performance, efficiency, and manufacturing cost has become very tight.

One of the main requirements is to guarantee the best possible reproducibility of the quantity of substance that is dispensed each time the inhaler is actuated. This is particularly crucial when the inhaler contains medication that must be dosed very accurately, as is particularly the case for medication against asthma.

Also, the quality of pulverization is likewise important in ensuring that the expelled dose of powder does not include any clumps of powder. Such clumps prevent the powder from diffusing properly in the lungs and consequently reduce the effectiveness of the product.

In general, powder inhalers comprise a metering chamber filled with powder, which metering chamber is emptied when the inhaler is actuated, either by a flow of compressed air, or else by a flow of air generated by the user inhaling. An example of one such known apparatus is disclosed, in particular, in document WO 93/18812, and is shown in part in FIGS. 1 to 3. FIGS. 1 to 3 are respectively a longitudinal section, a cross-section, and a horizontal section of a metering chamber 10 having an expulsion channel 20 passing therethrough extending to a mouthpiece 30 of the dispenser. The metering chamber 10 is filled with substance from a supply of the substance (not shown), and when the apparatus is in operation, a flow of air represented diagrammatically by arrows in FIGS. 1 and 3, passes along said expulsion channel 20 to empty the metering chamber 10 and bring the dose of substance to the mouthpiece 30 of the dispenser from which it is dispensed to the user.

To obtain good dose reproducibility, it is necessary both for the metering chamber to be refilled completely after each utilization, and also for it to be emptied completely each time the apparatus is actuated. If the metering chamber is not emptied completely, then the volume of the dose as expelled no longer corresponds to the prescribed dose, and the powder remaining in the metering chamber can form powder build-up zones that prevent good dose reproducibility.

In such an apparatus, expulsion of the powder dose, i.e. emptying of the metering chamber, is an operation that is very difficult to perform, and it depends on numerous parameters, including:

- the shape and the size of the metering chamber, and thus the quantity of medication to be dispensed;
- the shape of the expulsion duct, which often does not correspond to the shape of the metering chamber; thus, as can be seen in particular in FIG. 2, the metering chamber 10 is generally of cross-sectional area that is greater than that of the expulsion channel 20;
- the size of the expulsion duct, which needs to guarantee an appropriate air speed; and
- the air flow conditions which depend on the source of air and on the dimensions of the expulsion duct.

In known devices, as shown in FIGS. 1 to 3, the expulsion duct 20 is generally cylindrical, and the air flow matches the shape of the duct. Thus, when the air flow penetrates into the metering chamber 10 while it is filled with powder, the flow follows a trajectory that is substantially rectilinear between the inlet and the outlet of said metering chamber. Under such circumstances, particularly when the metering chamber is of large volume, the flow of air tends, initially, to “dig a tunnel” through the powder, i.e. to form a passage as shown in dashed lines in FIG. 3 extending directly from the inlet to the outlet of the metering chamber 10, with said passage corresponding substantially to an extension of the expulsion channel 20 through the metering chamber. In this way, only a portion of the powder contained in the metering chamber is expelled. Thereafter, in a second step, if the metering chamber is not too large, the air flow entrains powder situated around said “tunnel”.

Although that arrangement has been found to be effective for metering chambers that are relatively small, it suffers from considerable drawbacks when large doses are to be delivered. Under such circumstances, a portion of the powder lying in side zones of the metering chamber, i.e. zones in the vicinity of its walls, is not expelled and builds up in said chamber, thereby giving rise to problems of dose reproducibility.

As a result, increasing the volume of the metering chamber in such a prior art inhaler requires a corresponding adaptation of the expulsion channel and thus of the air flow source, thereby considerably increasing the cost of manufacturing such an apparatus.

In another known device, disclosed in document WO 95/28980, the metering chamber is defined in part by an insert that projects into the expulsion channel. That metering chamber also includes side zones that are difficult to empty. Furthermore, because of the presence of the insert projecting into the channel through a wall thereof, problems of powder retention can arise on the downstream portion of the insert, such that dose reproducibility is not guaranteed.

An object of the invention is to provide a device that makes it easier to empty a metering chamber for the purpose of accurately guaranteeing dose reproducibility.

Another object of the invention is to provide a device for making it easier to empty a metering chamber, in which the dose of powder is completely broken up while it is being expelled.

Documents U.S. Pat. No. 1,732,566 and U.S. Pat. No. 3,522,659 disclose devices including flow means for modifying the configuration of the air flow in the metering chamber in order to facilitate emptying. The means are disposed in the metering chamber in such a manner that modifying the dimensions of the metering chamber requires said flow means to be modified.

Thus, another object of the invention is to provide a device making it easier to empty a metering chamber in which it is possible to modify the volume of the metering chamber without the need to modify any other portion of the dispenser.

A further aim of the invention is to provide a device for making it easier to empty a metering chamber, and that also makes it possible to guarantee good dose reproducibility, independently of the volume of the metering chamber, and without increasing the manufacturing cost of the dispenser.

The invention thus provides a device for making it easier to empty a metering chamber of a powder dispenser, said dispenser including an expulsion channel passing through said metering chamber, and means for delivering an air flow which is intended, when the dispenser is actuated, to pass along said expulsion channel to empty said metering chamber, said device including flow means adapted to configure the air flow in such a manner that it empties said metering chamber completely, the device being characterized in that said flow means are disposed in the expulsion channel outside and upstream from said metering chamber in the flow direction of said air flow.

In particular, said metering chamber includes at least one portion of cross-sectional area greater than the cross-sectional area of said expulsion channel, forming at least one side zone, said flow means being adapted to direct at least a portion of the air flow into said at least one side zone of said metering chamber in such a manner as to empty said metering chamber completely, including in said at least one side zone.

The invention is thus adapted to modify the configuration of the air flow as its penetrates into the metering chamber, and in particular in such a manner that at least a portion of the air flow is directed towards said side zones to expel the dose in full, independently of the relationship between the cross-sectional area of the metering chamber and that of the expulsion channel. It is thus possible to make inhalers using metering chambers of various volumes and shapes without any need to modify other portions of the inhaler, which is of considerably economic advantage. Also, dose reproducibility is guaranteed completely in all of the various inhalers.

In a preferred embodiment of the invention, said flow means include an insert disposed in fixed manner in said expulsion channel. Since the insert is independent of the volume of the metering chamber, it therefore guarantees that it is emptied regardless of its volume. In particular, a change in the volume of the metering chamber does not require a change of insert.

In a first variant, said insert includes a solid central core, the air flow flowing over the outside surface of said central core.

In a second variant, said insert includes a central core having an axial opening along its longitudinal central axis, a portion of the air flow flowing through said axial orifice and the remainder flows along the outside surface of said central core.

In this way, the insert makes it possible to maintain the same air flow speed while increasing the contact area between the air flow and the powder contained in the metering chamber.

Preferably, said insert is dimensioned in such a manner as to be held in fixed manner by being jammed in the expulsion channel. When manufacturing an inhaler, it thus suffices to engage an insert of the invention; in general the insert is a very cheap and small piece of plastics or metal which is inserted into the expulsion channel upstream from the metering chamber. No additional step is required to fix the insert in the channel, where such a step would increase manufacturing costs.

In a particular embodiment of the invention, the expulsion channel is of circular or oblong cross-section, and said insert is of polygonal cross-section.

In another particular embodiment of the invention, the expulsion channel is polygonal in section and said insert is of circular or oblong cross-section.

In a preferred embodiment of the invention, said insert further includes at least one rib extending substantially axially along the outside surface of said central core.

Advantageously, the expulsion channel is of substantially circular cross-section, the core of the insert being of substantially circular cross-section, smaller than that of said expulsion channel, said insert including a plurality of ribs extending substantially axially along the outside surface of said central core, the outside diameter of the insert over said ribs being nearly identical to the inside diameter of said expulsion channel, such that the insert is held in said channel by jamming via said ribs.

Advantageously, the insert includes at least three ribs which are regularly distributed around the central core so that the central core is centered in the middle of said expulsion channel.

Preferably, the insert includes four identical ribs that are diametrically opposite in pairs around said central core.

In a first variant, said at least one rib extends axially over the central core parallel to the longitudinal axis of the expulsion channel.

In a second variant, said at least one rib extends axially over the central core in twisting manner about the longitudinal axis of the expulsion channel such that the insert establishes a turbulent air flow.

Preferably, the cross-section of the downstream end of said central core of the insert in the flow direction of the air flow is greater than the cross-section of the upstream end of said central core such that the insert establishes a flow of air that penetrates into the metering chamber on a conical path.

Optionally, said flow means include at least one groove or rib extending helically along the inside wall of the expulsion channel. In this variant, the insert may optionally be omitted, with the helical profile formed in the expulsion channel establishing the turbulent flow of air in the metering chamber.

In yet another advantageous embodiment, said metering chamber is defined in part by a metering element disposed in fixed manner in the expulsion channel, said metering element being disposed downstream from said flow means in the flow direction of said air flow.

Preferably, said metering element is disposed remotely from the walls of the expulsion channel in such a manner that the air flow flows over the entire periphery of said metering element. Thus, no powder can be retained on any portion of said metering element, and all of the dose is expelled on each actuation.

Advantageously, said metering element is terminated in a point at its downstream end in the air flow direction.

Preferably, said metering element is fixed to said flow means.

Advantageously, said flow means are implemented in the form of an insert fixed to a fixing member, said fixing member being fixed axially in line with the expulsion channel such that the insert projects into said expulsion channel away from the walls of said channel, the air flow flowing over the entire periphery of said insert. The insert may have any of the shape described above, and in particular, said insert is of rectangular cross-section and said metering element is of circular cross-section. Thus, the configuration of the air flow is modified by the insert, and said modified air flow includes turbulence because of the shape of the insert, thereby causing the metering chamber to be emptied completely. Because the air flow flows all around the periphery of the metering element, and because the metering element terminates at a point, it is guaranteed that the entire dose will be completely pulverized.

Preferably, said metering element, said insert, and said fixing member are made as a single piece. This implementation facilitates installing the device comprising the insert plus the metering element, and thereby reduces manufacturing and assembly costs. Also, in order to change the metering chamber, it suffices to change the metering element, without changing any other part of the apparatus in any way, and that too limits costs.

Advantageously, said metering element includes a zone, such as a cup, defining the volume of the metering chamber. Thus, to change the volume of the metering chamber, it suffices to change said zone of the metering element, which can be done very simply and at low cost.

Advantageously, said air flow is a flow of compressed air created in the dispenser by a prestressed pump device which is triggerable during actuation of the dispenser.

Other characteristics and advantages appear from the following detailed description given by way of non-limiting description and with reference to the accompanying drawings, in which:

FIG. 1 is a diagrammatic longitudinal section view of a metering chamber and an expulsion channel of a prior art inhaler;

FIG. 2 is a cross-section view of the FIG. 1 arrangement;

FIG. 3 is a horizontal section of the FIG. 1 arrangement;

Figure 5:
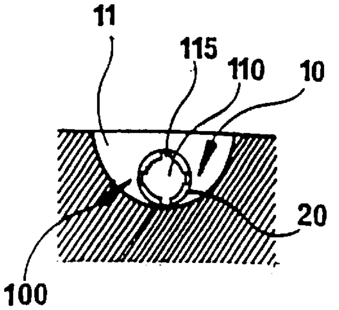
FIG. 5 is a view similar to FIG. 2, incorporating the insert of FIG. 4.
Figure 6B:
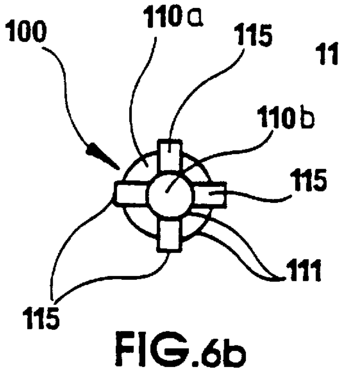
Figure 6A:
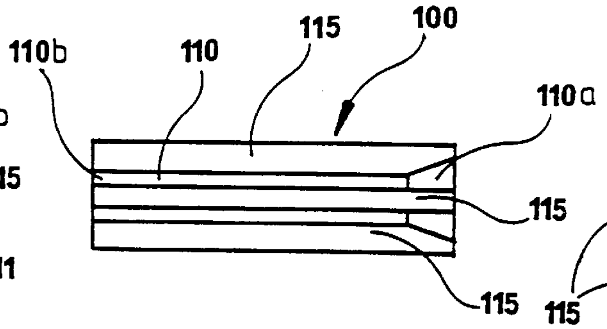
Figure 6C:
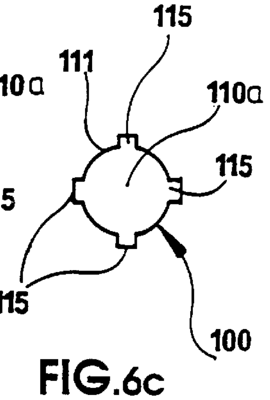
Figure 7:
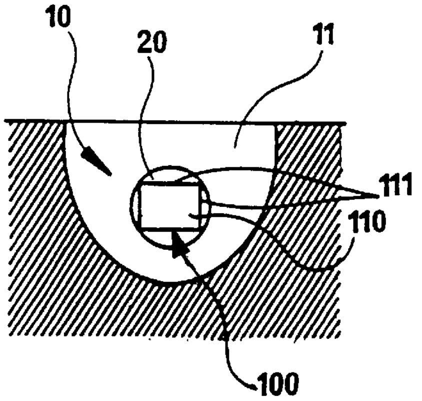
Figure 8:
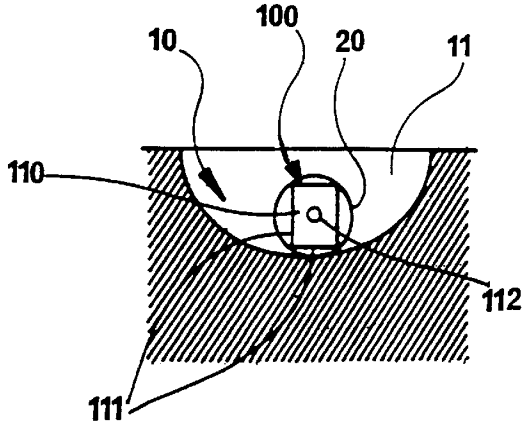
Figure 9:
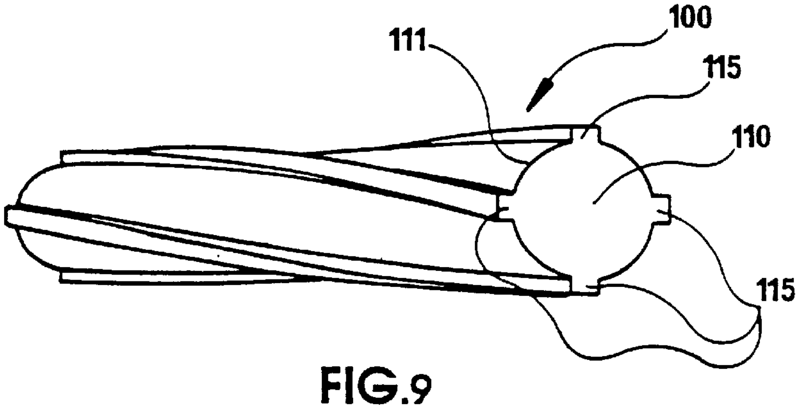
Figure 10:
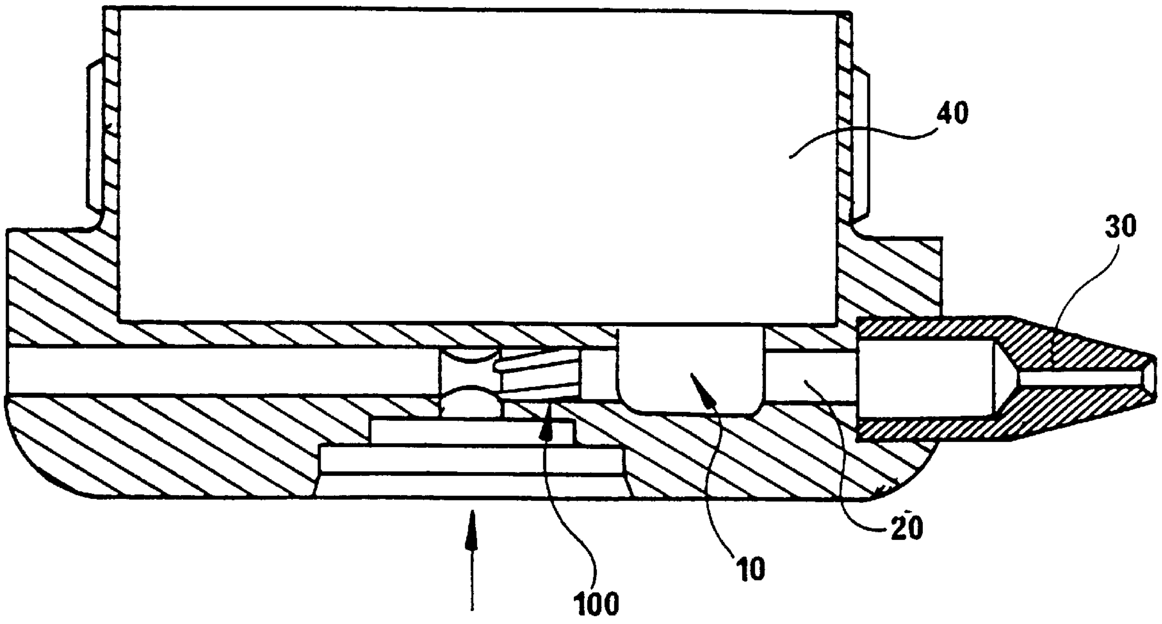
Figure 11:
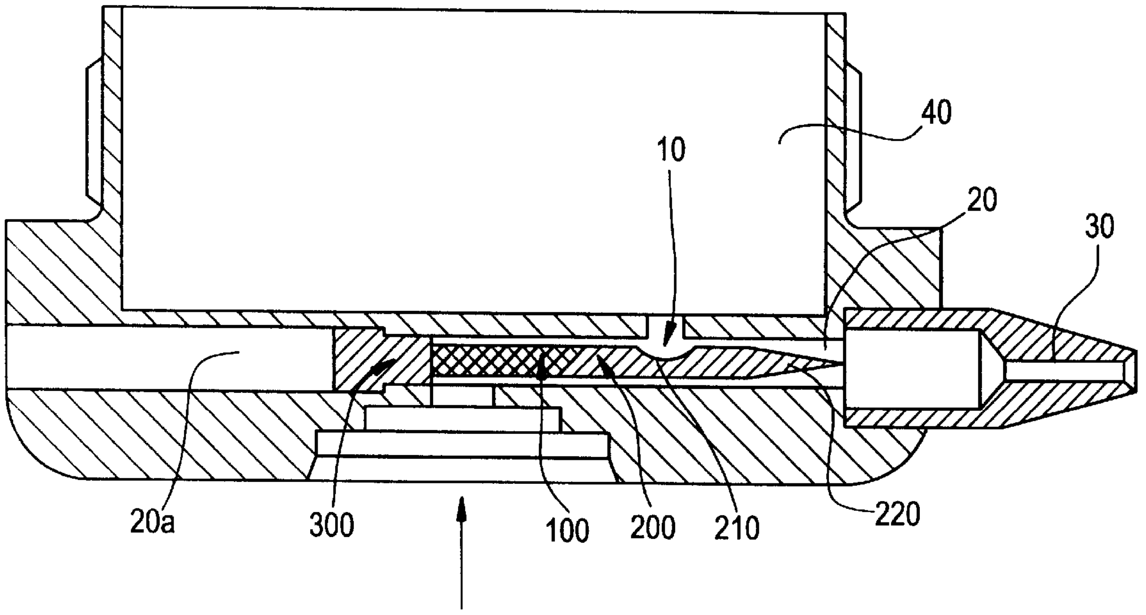
Figure 12A:
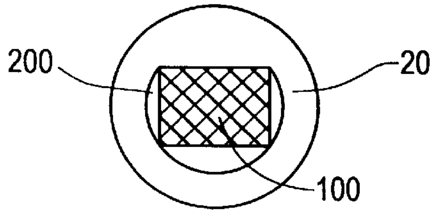
Figure 12B:
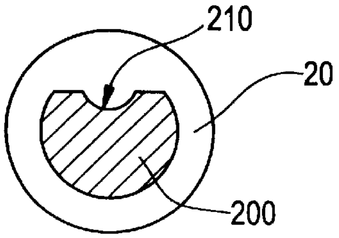

FIG. 6*a* is a diagrammatic longitudinal section of an insert in an advantageous embodiment of the invention;

FIG. 6*b* is a diagrammatic cross-section of the upstream end of the FIG. 6*a* insert;

FIG. 6*c* is a diagrammatic cross-section of the downstream end of the FIG. 6*a* insert;

FIG. 7 is a view similar to FIG. 5 incorporating an insert constituting a variant embodiment of the invention;

FIG. 8 is a view similar to FIG. 7, incorporating another variant insert of the invention;

FIG. 9 is a diagrammatic perspective view of an insert constituting another advantageous embodiment of the invention;

FIG. 10 is a diagrammatic view of a portion of a dispenser including the insert of FIG. 9;

FIG. 11 is a view similar to FIG. 10, incorporating a device constituting another embodiment of the invention; and FIGS. 12*a* and 12*b* are diagrammatic cross-section views respectively through the insert and through the metering element of the FIG. 11 device.

With reference to FIG. 10, a dispenser such as a powder inhaler comprises a metering chamber 10 designed to be filled with substance from a supply 40 via a filling mechanism (not shown). The metering chamber 10 has an expulsion channel 20 passing therethrough which extends one way towards a dispensing mouthpiece 30 of the inhaler, and the other way towards an air flow source (not shown). As can also be seen in FIG. 4, the invention provides for placing flow means such as an insert 100 in the expulsion channel 20 upstream from the metering chamber 10 in the air flow direction as represented diagrammatically by the arrows, which flow means are designed to improve emptying of the metering chamber when the dispenser is actuated. The insert 100 which is preferably fixed by being jammed in said expulsion channel 20, is designed to change the configuration of the air flow, and in particular its shape, as it penetrates into the metering chamber 10, and to do so in such a manner that said air flow is directed towards the side zones 11 of the metering chamber 10 lying outside the portion of the expulsion duct 20 which passes through said metering chamber 10. As can be seen in particular in FIGS. 4, 5, 7, and 8, the cross-section of the metering chamber 10 is generally of greater area than is the cross-section of the expulsion channel 20, so said side zones 11 are consequently portions of the metering chamber 10 that are situated in the vicinity of its sides. The insert 100 also makes it possible to establish turbulence or swirling in the air flow such that on penetrating into the metering chamber, the turbulence or swirling acts to break up the dose of powder, should that be necessary. In this way, the entire dose is expelled in optimum manner.

Figure 4:
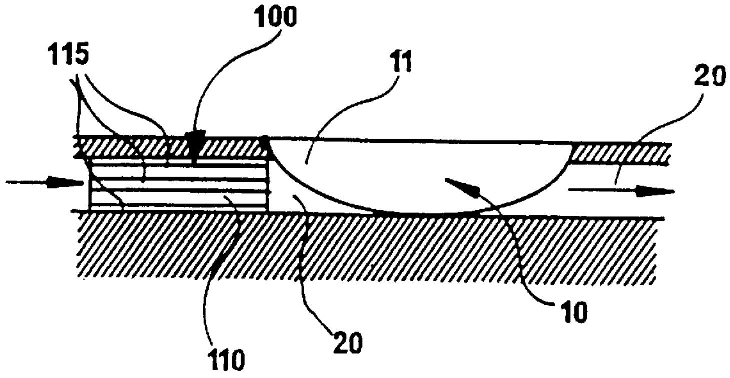
FIG. 4 is a view similar to that of FIG. 1, incorporating an insert constituting a first embodiment of the invention.

In accordance with the invention, the insert 100 comprises a central core 110 which extends preferably up to the entrance of said metering chamber 10. In a preferred embodiment of the invention, the expulsion channel and the central core 110 of the insert 100 are both of substantially circular cross-section, with the cross-section of the central core naturally being slightly smaller than the cross-section of said expulsion channel 20. The insert 100 is thus generally roughly cylindrical in shape. Preferably, the insert 100 also includes at least one rib 115 extending approximately axially along the outside surface 111 of said central core 110 of the insert 100. Advantageously, the insert includes at least three ribs 115 distributed around said central core 110, said ribs being made in such a manner that the outside diameter of the insert 100, over the ribs 115 is about the same or very slightly greater than the inside diameter of said expulsion channel 20, thereby making it possible to fix the insert 100 in the channel 20 by jamming via said ribs 115. With reference to FIGS. 4 and 5, the insert 100 has four identical ribs 115 extending parallel to the longitudinal axis of the insert. These ribs 115 are diametrically opposite in pairs about the central core 110 so that said central core 110 is centered in the middle of said expulsion channel 20. In this example, the central core 110 is solid so that the flow of air coming from the air flow source flows over the outside surface 111 of the central core 110 of the insert 100 between the various ribs 115.

In this way, the shape of the air flow which was substantially cylindrical prior to coming into contact with the insert 100, i.e. which matched the shape of the expulsion channel 20, is modified by the insert 100 so that when the air flow opens out into the metering chamber 10, it is substantially in the form of a hollow tube such that the active portion of the air flow is closer to the walls of the metering chamber 10 and is not directed directly towards the outlet of said metering chamber 10.

In an advantageous embodiment, shown in FIGS. 6*a*, 6*b*, and 6*c*, the insert 100 of generally cylindrical shape comprises a central core 110 whose cross-section at its upstream end 110*b* in the flow direction of the air flow, is smaller than its cross-section at its downstream end 110*a*. In this way, the air flow flowing along the outside surface 111 of the central core 110 of the insert 100 penetrates the metering chamber 10 with an air flow shape that is approximately frustoconical, flaring outwardly, such that said air flow is directed even more strongly towards the side zones 11 of the metering chamber 10 when it penetrates therein.

Another advantageous variant embodiment is shown in FIG. 9. As before, the insert 100, which is still generally cylindrical in shape, includes a central core 110 and four ribs 115 extending along its outside surface 111. In this variant, said ribs 115 extend over said outside surface 110 of the central core 110 in a manner that twists around the longitudinal axis of the central core 110 of the insert, which corresponds to the central longitudinal axis of the expulsion channel 20. In this way, the air flow flowing along said outside surface 111 of the central core 110, between the ribs 115, penetrates into the metering chamber with a swirling motion, thereby emptying it much more thoroughly. This is the variant of the insert 100 which is shown diagrammatically in the overall view of FIG. 10.

With reference to FIGS. 7 and 8, other variants of said insert 100 are shown diagrammatically. In this way, said central core 110 need not have ribs 115. In which case, if the expulsion channel 20 is of circular cross-section, the cross-section of the insert can be polygonal, preferably square or rectangular, so that it can be jammed in said expulsion channel 20 via its corners. As before, the air flow flows along the outside surface 111 of said central core 110. As shown in FIG. 8, said core 110 may also include an axial opening 112 extending along its central longitudinal axis, so that the air flow which reaches said insert 100 separates into a portion that flows axially through said axial opening 112, and a portion which flows over the outside surface 111 of said central core 110. When, as shown in FIGS. 7 and 8, the expulsion channel 20 is of circular cross-section and the insert 100 has a central core of rectangular cross-section, it is possible to change the distribution of the air flow over the four faces of said central core of generally rectangular shape, as a function of the shape of the metering chamber 10. Thus, when the metering chamber 10 is deeper than it is wide (FIG. 7), it is advantageous for the long sides of the insert 100 to extend horizontally, to deliver the larger portion of the air flow towards the top and bottom walls of the metering chamber 10. In contrast, when the metering chamber is wider than it is deep (FIG. 8), then the long sides of the rectangular parallelepiped 110 are advantageously disposed vertically so as to deliver the greatest portion of the air flow towards the side walls of the metering chamber 10. Naturally, any other polygonal shape for the cross-section of the insert 100 could be envisaged for obtaining the desired result, i.e. complete emptying of the metering chamber 10 by the air flow issued when the inhaler apparatus is actuated.

The various embodiments of the insert have been described with reference to an expulsion channel of cross-section that is substantially circular, however they can be applied equally to an expulsion channel of cross-section that is elliptical or oblong. Similarly, an expulsion channel of polygonal cross-section (in particular a section that is rectangular or square) can receive an insert in accordance with any one of the above-described embodiments of the invention. Also, if reference is made to the embodiments shown in FIGS. 7 and 8, the respective shapes of the cross-sections of the channel 20 and of the insert 100 can be interchanged, i.e. the expulsion channel 20 could be rectangular in cross-section, in which the case the insert 100 advantageously has a central core 110 of cross-section that is circular or elliptical.

Optionally, provision can be made for one or more grooves or ribs to extend helically along the inside wall of the expulsion channel. In which case, a portion of the air flow flows along said grooves or ribs so that a spinning air flow is created in the metering chamber. This can enable the insert to be omitted.

In another preferred embodiment of the invention, as shown in FIGS. 11, 12*a*, and 12*b*, the metering chamber 10 is partially defined by a metering element 200, in particular by means of a zone that defines the volume of said metering chamber. The zone 210 can be made in the form of a cup, as shown in FIGS. 11 and 12*b*, however it could equally well be arbitrary in shape, e.g. in the form of a mere flat supporting the quantity of powder that is fed from the supply 40. In accordance with the invention, said metering element 200 is fixed in the expulsion channel 20, downstream from said insert 100. The metering element 200 is preferably fixed in the expulsion channel 20 at a distance from the walls of said channel so that the air flow flows over its entire periphery. In this way, the air flow expels all of the powder since no powder retention can occur against a portion of said metering element 200. For even greater improvement thereof, the downstream end 220 of the metering element 200 advantageously terminates in a point.

Preferably, as shown in FIG. 11, the metering element 200 is fixed to the element 100, which is itself advantageously fixed to a fixing member 300. This fixing member 300 is fixed on the axis 20*b* of the expulsion channel 20, e.g. by jamming or by anchoring. Thus, the insert 100 and the metering element 200 project axially into the expulsion channel 20. The insert 100 is preferably also disposed remotely from the walls of the channel 20 so that the air flow flows around the entire periphery of the insert 100. In an advantageously embodiment of the invention, the fixing member 300, the insert 100, and the metering element 200 are made as a single piece, preferably of plastics material. Manufacture and assembly of the device of the invention are thus made very simple and therefore of very low cost, and a modification to the metering chamber, e.g. of its volume, can be implemented very easily while modifying only said metering element 200.

Preferably, as shown in FIGS. 12*a* and 12*b*, the cross-section of the insert 100 is substantially rectangular, while that of the metering element 200 is substantially circular. Thus, the insert 100 changes the configuration of the air flow and the transition between the insert and the metering element 200 therefore further enhances the creation of turbulence, such that it is guaranteed that the entire quantity of powder will be expelled in finely-divided form.

The various characteristics described above with reference to the various embodiments of the invention can Naturally be combined with one another in any manner without going beyond the ambit of the invention.

We claim:

1. A powder dispenser comprising:

a metering chamber (10);

an expulsion channel (20) passing through said metering chamber (10); and means for delivering an air flow intended, when the dispenser is actuated, to pass along said expulsion channel (20) to empty said metering chamber (10), flowing means (100) adapted to configure the air flow in such a manner that it empties said metering chamber (10) completely, and wherein said flowing means (100) is disposed in the expulsion channel (20) outside and upstream from said metering chamber (10) in the flow direction of said air flow, wherein said flowing means is independent of the dimensions of said metering chamber, wherein said metering chamber (10) includes at least one portion of cross-sectional area greater than the cross-sectional area of said expulsion channel (20), forming at least one side zone (11), said flowing means (100) being adapted to direct at least a portion of the air flow into said at least one side zone (11) of said metering chamber (10) in such a manner as to empty said metering chamber (10) completely including in said at least one side zone.

2. A powder dispenser according to claim 1, in which said flowing means (100) include an insert (100) disposed in a fixed manner in said expulsion channel.

3. A powder dispenser according to claim 2, in which said insert (100) includes a solid central core (110), the air flow flowing over an outside surface (111) of said central core (110).

4. A device according to claim 2, in which said insert (100) includes a central core (110) having an axial opening (112) along its longitudinal central axis, a portion of the air flow flowing through said axial opening (112) and the remainder flows along an outside surface (111) of said central core (110).

5. A powder dispenser according to claim 2, in which said insert (100) is dimensioned in such a manner as to be held in fixed manner by being jammed in the expulsion channel (20).

6. A powder dispenser according to claim 2, in which the expulsion channel (20) is of circular or oblong cross-section, and said insert (100) is of polygonal cross-section.

7. A powder dispenser according to claim 2, in which the expulsion channel (20) is polygonal in section and said insert (100) is of circular or oblong cross-section.

8. A powder dispenser according to claim 2, in which said insert (100) further includes at least one rib (115) extending substantially axially along an outside surface (111) of a central core (110).

9. A powder dispenser according to claim 8, which the expulsion channel (20) is of substantially circular cross-section, the core (110) of the insert (100) being of substantially circular cross-section, smaller than that of said expulsion channel (20), said insert (100) including a plurality of ribs (115) extending substantially axially along the outside surface (111) of said central core (110), the outside diameter of the insert (100) over said ribs (115) being nearly identical to the inside diameter of said expulsion channel (20), such that the insert (100) is held in said channel (20) by jamming via said ribs (115).

10. A powder dispenser according to claim 8, in which the insert (100) includes at least three ribs (115) which are regularly distributed around the central core (110) so that the central core (110) is centered in the middle of said expulsion channel (20).

11. A powder dispenser according to claim 8, in which the insert (100) includes four identical ribs (115) that are diametrically opposite in pairs around said central core (110).

12. A powder dispenser according to claim 8, in which said at least one rib (115) extends axially over the central core (110) parallel to the longitudinal axis of the expulsion channel (20).

13. A powder dispenser according to claim 8, in which said at least one rib (115) extends axially over the central core (110) in a twisting manner about the longitudinal axis of the expulsion channel (20) such that the insert (100) establishes a turbulent air flow in the metering chamber (10).

14. A powder dispenser according to claim 2, in which the cross-section of the downstream end (110*a*) of a central core (110) of the insert (100) in the flow direction of the air flow is greater than the cross-section of the upstream end (110*b*) of said central core (110) such that the insert (100) establishes a flow of air that penetrates into the metering chamber (10) on a conical path.

15. A powder dispenser according to claim 1, in which said flowing means (100) includes at least one groove or rib extending helically along an inside wall of the expulsion channel (20).

16. A powder dispenser according to claim 1, in which said metering chamber (10) is defined in part by a metering element (200) disposed in fixed manner in the expulsion channel (20), said metering element (200) being disposed downstream from said flowing means (100) in the flow direction of said air flow.

17. A powder dispenser according to claim 16, in which said metering element (200) is disposed remotely from the walls of the expulsion channel (20) in such a manner that the air flow flows over the entire periphery of said metering element (200).

18. A powder dispenser according to claim 16, in which said metering element (200) is terminated in a point (220) at its downstream end in the air flow direction.

19. A powder dispenser according to claim 16, in which said metering element (200) is fixed to said flowing means (100).

20. A powder dispenser according to claim 19, in which said flowing means (100) are implemented in the form of an insert (100) fixed to a fixing member (300), said fixing member (300) being fixed axially in line (20*a*) with the expulsion channel (20) such that the insert (100) projects into said expulsion channel (20) away from the walls of said channel (20), the air flow flowing over the entire periphery of said insert (100).

21. A powder dispenser according to claim 20, in which said insert (100) is of rectangular cross-section and said metering element (200) is of circular cross-section.

22. A powder dispenser according to claim 20, in which said metering element (200), said insert (100), and said fixing member (300) are made as a single piece.

23. A powder dispenser according to claim 16, in which said metering element (200) includes a zone (210), formed as a cup, defining the volume of the metering chamber (10).

24. A powder dispenser according to claim 1, in which said air flow is a flow of compressed air created in the dispenser by a prestressed pump device which is triggerable during actuation of the dispenser.

* * * * *